United States Patent [19]

Adger et al.

[11] Patent Number: 4,526,974

[45] Date of Patent: Jul. 2, 1985

[54] SYNTHESIS OF 2-PYRIDYLALKYLAMINES

[75] Inventors: Brian M. Adger, Hildenborough, Nr. Tonbridge, England; Antonietta R. Mastrocola, Bala Cynwyd, Pa.

[73] Assignee: Smith Kline & French Laboratories Limited, Welwyn Garden City, England

[21] Appl. No.: 477,036

[22] Filed: Mar. 22, 1983

[30] Foreign Application Priority Data

Mar. 25, 1982 [GB] United Kingdom ............... 8208750
May 20, 1982 [GB] United Kingdom ............... 8214723

[51] Int. Cl.$^3$ .......................................... C07D 213/38
[52] U.S. Cl. .................... 546/329; 546/296; 546/297; 546/300; 546/304; 546/307; 546/311
[58] Field of Search ............. 546/307, 311, 304, 296, 546/297, 300, 329

[56] References Cited

U.S. PATENT DOCUMENTS 4,154,834 5/1979 Brown et al. .................. 424/251
4,255,428 3/1981 Brown et al. .................. 424/251

FOREIGN PATENT DOCUMENTS 0068833 5/1983 European Pat. Off. .
0068834 5/1983 European Pat. Off. .
289905 7/1953 Switzerland .
1564503 4/1980 United Kingdom .

OTHER PUBLICATIONS

Vaughan et al., J. Org. Chem., 26, pp. 138–144, (1961).
Raynolds et al., J. Am. Chem. Soc., 82:1152–5, (1960).
Klingsberg, E. ed., "The Chemistry of Heterocyclic Compounds, Pyridine and Its Derivatives," Part Three, p. 71, (John Wiley & Sons, 1963).
Chemical Abstracts, 63:584c, (1965).
Marion et al., J. Am. Chem. Soc., 71:3402–4, (1949).
Kyte et al., J. Chem. Soc., 4454–4472, (1960).

Primary Examiner—Henry R. Jiles
Assistant Examiner—Bernard I. Dentz
Attorney, Agent, or Firm—Joan S. Keps; Richard D. Foggio; Alan D. Lourie

[57] ABSTRACT

The invention provides a process for preparing 2-pyridylalkylamines by reacting an alkali metal derivative of a 2-methylpyridine with a haloalkylamine. The compounds are useful as intermediates in the preparation of compounds having histamine $H_1$- and $H_2$-antagonist activity.

10 Claims, No Drawings

SYNTHESIS OF 2-PYRIDYLALKYLAMINES

This invention relates to a process for preparing 2-pyridylalkyl amines.

U.S. Pat. No. 4,154,834 discloses compounds of general formula (I):

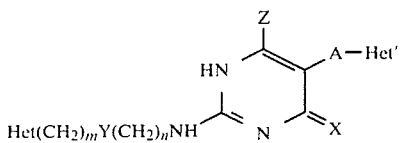

where inter alia, Het can be 2-pyridyl optionally substituted by one or two groups (which may be the same or different) selected from lower alkyl (preferably methyl), lower alkoxy (preferably methoxy), halogen (particularly bromine) and amino; Y can be a methylene group; m can be 0, 1 or 2 and n can be 2 or 3 such that their sum is 2, 3 or 4.

These compounds are described as having combined histamine $H_1$- and $H_2$- antagonist activity.

European Pat. Specification No. 0068833 and European Pat. Specification No. 0068834 disclose compounds of formula (Ia):

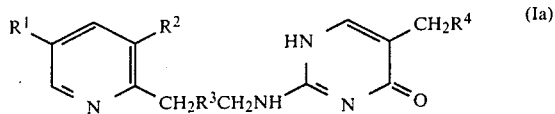

where, in Specification No. 0068833, $R^1$ is halogen or nitro; $R^2$ is $C_{1-4}$ alkyl; in Specification No. 0068834 $R^1$ is $C_{1-4}$ alkyl; $R^2$ is $C_{1-4}$ alkyl, $C_{3-4}$ alkoxy, halogen, or amino; and both Specifications $R^3$ is $C_{1-3}$ alkylene and $R^4$ represents certain specified substituted and unsubstituted 3- and 4- pyridyl groups. These compounds are useful as histamine $H_1$-antagonists.

The 2-pyridylalkyl amines which can be prepared by the process of this invention can be used to prepare certain compounds of formulae (I) and (Ia).

According to the present invention there is provided a process for preparing a compound of formula (II):

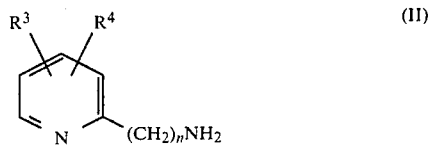

and salts thereof, where $R^3$ and $R^4$ are the same or different and are hydrogen, $C_{1-4}$ alkyl, $C_{1-4}$ alkoxy, amino or nitro and n is from 2 and 5, which comprises reacting an alkali metal derivative of a compound of formula (III):

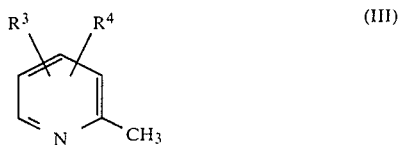

where $R^3$ and $R^4$ are as defined with reference to formula (II) with a compound of formula (IV):

$$X(CH_2)_{(n-1)}NH_2 \quad (IV)$$

or a salt thereof where X is halogen and n is as defined with reference to formula (II) in the presence of a non-interfering solvent, and thereafter optionally converting the compound of formula (II) so obtained into a salt.

Examples of $C_{1-4}$ alkyl groups which $R^3$ or $R^4$ represent are methyl, ethyl, n-propyl and n-butyl. Examples of $C_{1-4}$ alkoxy groups which $R^3$ or $R^4$ represent are methoxy, ethoxy, n-propoxy and n-butoxy.

In particular $R^3$ and $R^4$, when they are other than hydrogen, occupy positions 5 and 3 respectively of the pyridine ring.

Preferably $R^3$ is hydrogen and $R^4$ occupies position 3 of the pyridyl moiety and is $C_{1-4}$ alkyl. In particular it is methyl.

In particular n is 3 or 4.

In the compound of formula (IV) X can be chlorine, bromine or iodine. In particular it is chlorine.

Preferably an acid addition salt of a compound of formula (IV) is used, for example an addition salt with sulphuric or hydrochloric acid. Preferably the salt is the hydrochloride.

The alkali metal derivative can be a lithium, sodium or potassium derivative. In particular it is the sodium derivative.

Herein a non-interfering solvent means one which is substantially inert to the reagents or the products. The alkali metal derivative of the compound of formula (III) can be prepared in situ by reacting the compound of formula (III) with an alkali metal amide (in particular sodamide, where the alkali metal is sodium) in which case the solvent is preferably liquid ammonia, or an alkyl alkali metal (in particular butyl lithium, where the alkali metal is lithium) in which case the solvent is preferably an ether, for example diethyl ether or tetrahydrofuran.

Preferably the alkali metal derivative of the compound of formula (III) is prepared in situ in the presence of the compound of formula (IV). That is the alkali metal amide or the alkyl alkali metal is added to a mixture of the compound of formula (III) and the compound of formula (IV).

The reaction is carried out at a moderate to low temperature. For example where the alkali metal derivative of the compound of formula (III) is generated in situ from an alkali metal amide in liquid ammonia, the reaction is carried out at or below the boiling point of liquid ammonia. Where the alkali metal derivative of the compound of formula (III) is generated in situ from an alkyl alkali metal, the reaction is carried out at from room temperature to $-78°$ C. and preferably in an inert atmosphere.

Preferably the alkali metal derivative of the compound of formula (III) is the sodium derivative and is prepared from the compound of formula (III) and sodamide in liquid ammonia.

The product, that is the compound of formula (II), can be isolated from the reaction mixture by methods analogous to known methods and purified by standard techniques.

The compounds of formula (III) and (IV) are known or can be made by known methods.

The following Examples illustrate the invention.

EXAMPLES

EXAMPLE 1

2,5-Dimethylpyridine (321 g) is added to a solution of sodamide (351 g) in liquid ammonia (3 l) and the mixture is stirred for 1 hour. 1-Amino-3-chloro- propane hydrochloride (429 g) is added to the stirred solution over approximately 8 minutes with stirring. After this addition, any liquid ammonia lost through evaporation is replaced.

The reaction is quenched after 2 hours by the addition, with stirring, of ammonium chloride (120 g) to the reaction mixture. The ammonia is allowed to evaporate and after allowing the residue to stand (ca 16 hr), water (2 l), is added and the aqueous phase so obtained is extracted with dichloromethane and dried ($Na_2SO_4$).

The dichloromethane is evaporated and the residue is distilled in vacuo giving 4-(5-methyl-2-pyridyl)butylamine.

EXAMPLE 2

2,3-Lutidine (321 g) was added with stirring to a solution of sodamide (351 g) in liquid ammonia (3 l). 1-Amino-3-chloropropane hydrochloride (429g) was added to this mixture over 8 minutes with stirring. Any liquid ammonia lost through evaporation was replaced. After 2 hours the reaction was quenched by the addition of ammonium chloride (120 g) and the reaction mixture was left to stand overnight to allow substantially complete escape of ammonia through evaporation. The residue so obtained was diluted with water (2 l) and extracted with dichloromethane. The extracts were dried ($Na_2SO_4$), the dichloromethane removed by evaporation and the residue distilled in vacuo to give 4-(3-methyl-2-pyridyl) butylamine (306.6 g).

EXAMPLE 3

3-Methoxy-2-methylpyridine (369 g) was added to a solution of sodamide (351 g) in liquid ammonia (3 l) and the mixture was stirred for 1 hour. 1-Amino-3-chloro-propane hydrochloride (429 g) was added to the stirred solution over approximately 7 minutes. After this addition, any liquid ammonia lost through evaporation was replaced.

The reaction was quenched after 5.5 hours by the addition, with stirring, of ammonium chloride (120 g) to the reaction mixture. The ammonia was allowed to evaporate and after allowing the residue to stand (ca 6 hr), water (2 l), was added and the aqueous phase so obtained was extracted with dichloromethane and dried ($Na_2SO_4$).

The dichloromethane was evaporated and the residue distilled to give 4-(3-methoxy-2-pyridyl)butylamine (322.4 g) b.p.$_{0.05}$ mm 110–114° C.

EXAMPLE 4

Substituting 4-methoxy-2-methylpyridine (369 g) for 3-methoxy-2-methylpyridine in the process of Example 3 gives 4-(4-methoxy-2-pyridyl)butylamine.

EXAMPLE 5

Substituting 5-methoxy-2-methylpyridine (369 g) for 3-methoxy-2-pyridine in the process of Example 3 gives 4-(5-methoxy-2-pyridyl)butylamine.

EXAMPLE 6

Substituting 3,5-dimethoxy-2-methylpyridine (459 g) for 3-methoxy-2-methylpyridine in the process of Example 3 gives 4-(3,5-dimethoxy-2-pyridyl)butylamine.

EXAMPLE 7

Substitution of 5-nitro-2-methylpyridine (414 g) for 3-methoxy-2-methylpyridine in the process of Example 3 gives 4-(5-nitro-2-pyridyl)butylamine.

EXAMPLE 8

Sodamide (58.5 g) was added over 5 min with stirring to a solution of 2-methyl-3-methoxypyridine in liquid ammonia (II). The reaction mixture was stirred for 50 min and then quenched with ammonium chloride (64.2 g). The liquid ammonia was evaporated and the residue was diluted with water (500 ml). The diluted residue was taken to pH 14 with aqueous sodium hydroxide solution (50% w/v). The organic portion was extracted with dichloromethane, the extract dried ($MgSO_4$) and the solvent evaporated. The residue was distilled in vacuo to yield 4-(3-methoxy-2-pyridyl)butyl amine (61.8 g; b.p.$_{0.3}$ 110–111° C).

What is claimed is:

1. A process for preparing a compound of formula (II):

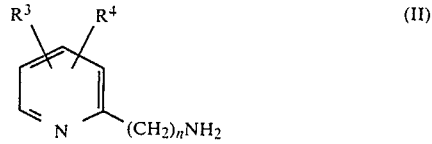

where $R^3$ and $R^4$ are the same or different and are hydrogen, $C_{1-4}$ alkyl, $C_{1-4}$ alkoxy, amino or nitro and n is 3 or 4 which comprises reacting an alkali metal derivative of a compound of furmula (III):

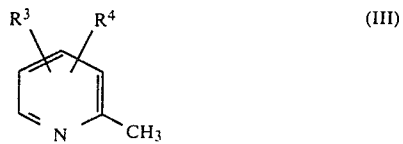

where $R^3$ and $R^4$ are as defined with reference to formula (II) with a compound of formula (IV):

$$X(CH_2)_{(n-1)}NH_2 \qquad (IV)$$

which is used in the form of an acid addition salt thereof, where n is defined with reference to formula (II) and X is halogen, in the presence of a non-interfering solvent, and thereafter optionally converting the compound of formula (I) so obtained into a salt.

2. A process according to claim 1, where $R^3$ is hydrogen and $R^4$ is in position 3 of the pyridine ring and is $C_{1-4}$ alkyl.

3. A process according to claim 2, where $R^4$ is methyl.

4. A process according to claims 1, 2 or 3 where n is 3.

5. A process according to claim 1 where X is chlorine.

6. A process according to claim 1 where the salt is a hydrochloride salt.

7. A process according to claim 1 where the alkali metal derivative of the compound of formula (III) is formed in situ from an alkali metal amide or an alkyl alkali metal.

8. A process according to claim 7 where the alkali metal derivative of the compound of formula (III) is prepared in situ in the presence of the compound of formula (IV).

9. A process according to claims 7 or 8 where the alkali metal amide is sodamide.

10. A process according to claims 1, 2 or 3 where n is 4.

* * * * *